(12) United States Patent
Sugihara et al.

(10) Patent No.: US 7,794,748 B2
(45) Date of Patent: Sep. 14, 2010

(54) STABLE ORAL SOLID DRUG COMPOSITION

(75) Inventors: Akio Sugihara, Shizuoka (JP);
Katsuhiro Masaki, Shizuoka (JP);
Takehiko Yasuji, Shizuoka (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 414 days.

(21) Appl. No.: 10/928,464

(22) Filed: Aug. 27, 2004

(65) Prior Publication Data

US 2005/0026981 A1 Feb. 3, 2005

Related U.S. Application Data

(63) Continuation of application No. PCT/JP2004/000896, filed on Jan. 30, 2004.

(30) Foreign Application Priority Data

Jan. 31, 2003 (JP) .............................. 2003-023500

(51) Int. Cl.
*A61K 9/20* (2006.01)
(52) U.S. Cl. ...................... 424/464; 424/465
(58) Field of Classification Search .................. 424/464
See application file for complete search history.

(56) References Cited

U.S. PATENT DOCUMENTS

| | | | |
|---|---|---|---|
| 4,067,974 A | 1/1978 | Sasmor | |
| 4,839,176 A | 6/1989 | Pankhania et al. | |
| 5,223,508 A | 6/1993 | Izawa et al. | |
| 5,344,927 A | 9/1994 | Ohta et al. | |
| 6,284,770 B1 | 9/2001 | Mangel | |
| 6,297,244 B1 | 10/2001 | Ohashi | |
| 6,372,755 B2 | 4/2002 | Hanamura | |
| 2001/0004637 A1 | 6/2001 | Hanamura et al. | |
| 2002/0040033 A1 | 4/2002 | Cautreels et al. | |
| 2002/0150624 A1 | 10/2002 | Watanabe et al. | |
| 2003/0143548 A1 | 7/2003 | Camilleri et al. | |
| 2005/0026981 A1 | 2/2005 | Sugihara et al. | |
| 2005/0192329 A1 | 9/2005 | Nishida et al. | |
| 2007/0037866 A1 | 2/2007 | Nishida et al. | |

FOREIGN PATENT DOCUMENTS

| | | | |
|---|---|---|---|
| CN | 1237106 A | | 12/1999 |
| CN | 1282247 A | | 1/2001 |
| EP | 0 274 845 | | 7/1988 |
| EP | 1021174 | | 7/2000 |
| EP | 1 205 190 A1 | * | 5/2002 |
| EP | 1302201 | | 4/2003 |
| EP | 1 413 294 A1 | | 4/2004 |
| JP | 63-165320 | | 7/1988 |
| JP | 5-6226 | | 3/1999 |
| JP | 2001-518495 | | 10/2001 |
| WO | 99/17755 | * | 4/1999 |
| WO | WO 99/17755 | | 4/1999 |
| WO | WO-01/10446 | | 2/2001 |
| WO | WO-02/05786 | | 1/2002 |
| WO | WO-03/013482 A1 | | 2/2003 |

OTHER PUBLICATIONS

Japanese Pharmaceutical Excipients Dictionary, First Edition, compiled by Japan Pharmaceutical Excipients Council and published by Yakuji Nippo, Ltd. (Jan. 14, 1994), p. 2, "Ascorbic Acid" section; p. 3, "L-Aspartic Acid" section; p. 18 "Erythorbic Acid" section; pp. 38 to 39, "Citric Acid" section; p. 65, "Tartaric Acid" section; p. 113, "Fumaric Acid" section; p. 117, "Propyl Gallate" section.

K. Masaki et al., Kagakuryoho no Ryoiki, 14(11):2004-2008 (1998).

T. Kuwabara et al., J. Gastroenterol., 29:721-726 (1994).

N. Kishibayashi et al., J. Med. Chem., 36:3286-3292 (1993).

Japan Pharmaceutical Reference, The Fifth Edition (1999), Nasea Injection 0.3 mg (p. 1278-1280) and Nasea OD Tablets 0.1 mg (p. 1281-1283).

M. Schubert-Zsilavecz et al. Das Reizdarmsyndrom Irritable Bowel Syndrome, Deutsche Apotheker Zeitung, Stuttgart, DE, vol. 142, No. 34, Aug. 22, 2002, 40-49, XP001182359.

Ramosetron hydrochloride, *Drugs of the Future*, vol. 21, No. 1, 1996, 116-116, XP009047048.

A. Ozaki et al. Effect of the 5-hydroxytryptamine$_3$ (5-ht$_3$)-receptor antagonist KB-R6933 on experimental diarrhea models, *Jpn. J. Pharmacol.*, vol. 80, 1999, 93-96, XP009047033.

H. Ito, et al. Investigation of the effects of YM-31636, a novel 5-ht$_3$ receptor agonist, on defecation in normal and constipated ferrets, European Journal of Pharmacology, vol. 424, 2001, 151-157, XP002326683.

C. Steadman et al. Selective 5-Hydroxytryptamine Type 3 Receptor Antagonism with Ondansetron as Treatment for Diarrhea-Predominant Irritable Bowel Syndrome: A Pilot Study, Mayo Clinic Proceedings, Mayo Medical Ventures, Rochester, MN, US, vol. 67, No. 8, Aug. 1992, 732-738, XP002098638.

(Continued)

*Primary Examiner*—Humera N Sheikh
(74) *Attorney, Agent, or Firm*—Edwards Angell Palmer & Dodge LLP

(57) ABSTRACT

This invention is aimed to provide a stabilized formulation of ramosetron or a pharmaceutically acceptable salt thereof under a temperature/humidity condition, especially at a low content and relates to a stable oral solid drug composition of ramosetron or a pharmaceutically acceptable salt thereof, which is characterized by containing one or two or more members selected from the group consisting of an aliphatic carboxylic acid or an ester thereof, a hydroxycarboxylic acid or an ester thereof, an acidic amino acid, an enolic acid, an aromatic carboxyl compound or an ester thereof, and a carboxyl group-containing high-molecular substance, and to a stabilization method of the same. Also, this invention relates to a therapeutic agent of diarrhea-predominant irritable bowel syndrome containing from 0.002 to 0.02 mg of ramosetron hydrochloride as a daily dose or an equivalent molar amount of ramosetron or its pharmaceutically acceptable other salt as an active ingredient.

27 Claims, No Drawings

OTHER PUBLICATIONS

G. Stacher et al. Effects of the 5-$HT_3$ Antagonist Cilansetron vs Placebo on Phasic Sigmoid Colonic Motility in Healthy Man: a Double-Blind Crossover Trial, British Journal of Clinical Pharmacology, Blackwell Scientific Publ, GB, vol. 49, No. 5, 2000, 429-436, XP001058300.

T. Hirata et al., Usefulness of 5-HT3 receptor antagonists in irritable bowel syndrome—pharmacological profile of ramosetron hydrochloride, *Saibo*, 2003, vol. 35, No. 10 p. 398-401.

M. Ohta et al., Chem. Pharm. Bull., 44(5):991-999 (1996).

M. Ohta et al., Chem. Pharm. Bull., 44(5):1000-1008 (1996).

M. Ohta et al., Chem. Pharm. Bull., 44(9):1707-1716 (1996).

M. Ohta et al., Chem. Pharm. Bull., 44(9):1717-1722 (1996).

K. Miyata et al., Journal of Pharmacology and Experimental Therapeutics, 261(1):297-303 (1992).

K. Miyata et al., American Physiological Society, pp. G827-G831 (1998).

Kikuta et al., Japanese Journal of Pediatrics, 52:425-432 (1999).

Noda et al., Japanese Journal of Clinical and Experimental Medicine, 71(10):2753-2764 (1994).

Nakajima et al., The Japanese Journal of Clinical and Experimental Medicine, 71(9):2461-2468 (1994).

Sekino et al., Japanese Pharmacology and Therapeutics, 22(9):3877-3888 (1994).

Noda et al., The Japanese Journal of Clinical and Experimental Medicine, 71(10):2765-2776 (1994).

Noda et al., Journal of New Remedies & Clinics, 43(11):2241-2255 (1994).

Taketani et al., The World of Obstetrics and Gynecology, 46(12):965-973 (1994).

Taketani et al., Obstetrics & Gynecology, 61(12):1759-1770 (1994).

Kawabata et al., Nishinihon Journal of Urology, 56:1445-1456 (1994).

Mori et al., The Journal of Adult Diseases, 24(12):2257-2265 (1994).

Sato et al., Japan Journal of Cancer Clinics, 50(4):305-313 (2004).

Noda et al., Journal of New Remedies & Clinics, 45(7):1309-1321 (1996).

Noda et al., Journal of New Remedies & Clinics, 45(3):482-490 (1996).

Taketani et al., Obstetrics & Gynecology, 63(9):1297-1308 (1996).

Taketani et al., The World of Obstetrics and Gynecology, 48(8)749-760 (1996).

Noda et al., Journal of New Remedies & Clinics, 45(8):1445-1462 (1996).

Office Action dated May 26, 2009, issued in the corresponding Indian patent application.

* cited by examiner

STABLE ORAL SOLID DRUG COMPOSITION

This application is a continuation of International Application PCT/JP04/000896, filed Jan. 30, 2004 and designated the United States, and which is incorporated herein by reference in its entirety.

TECHNICAL FIELD

The present invention relates to a stable oral solid drug composition of ramosetron or a pharmaceutically acceptable salt thereof, which is characterized by containing a specific compound having a carbonyl group. Also, this invention relates to a stabilization method of an oral solid drug composition of ramosetron or a pharmaceutically acceptable salt thereof, which is characterized by compounding a specific compound having a carbonyl group. Also, this invention relates to a novel therapeutic method of diarrhea-predominant irritable bowel syndrome.

BACKGROUND ART

A chemical name of ramosetron is (−)-(R)-5-[(1-methyl-1H-indol-3-yl)carbonyl]carbonyl-4,5,6,7-tetra-hydro-1H-benzimidazole. A series of tetrahydrobenzimidazole derivatives including said ramosetron and pharmaceutically acceptable salts thereof are reported as a useful drug compound having an excellent antagonistic action against a serotonin (5-$HT_3$) receptor and suppressing diseases of digestive tract induced by administration of anticancer agents, such as nausea and vomiting (see Patent Document 1), and in particular, a hydrochloride of ramosetron is already marketed (hereinafter, the marketed drug compound will be referred to as "ramosetron hydrochloride"). It is known that the ramosetron hydrochloride exhibits an excellent pharmacological effect against adults upon its oral administration of 0.1 mg once a day, and it is on sale as a trade name of "Nasea OD Tablets 0.1 mg" from Yamanouchi Pharmaceutical Co., Ltd.

Also, in view of the fact that serotonin receptor antagonists irritate a serotonin (5-$HT_3$) receptor and increase liberation of acetylcholine, they are expected to be applicable as a therapeutic agent of irritable bowel syndrome (IBS). However, a few of serotonin receptor antagonists are clinically confirmed to have a therapeutic effect against patients of irritable bowel syndrome, and with respect to the ramosetron hydrochloride, its effectiveness has not been reported yet.

The present inventors obtained an idea that an effective amount of ramosetron hydrochloride for therapy against irritable bowel syndrome may possibly be far low as compared with 0.1 mg as the administration amount that is currently employed for a depressor of diseases of digestive tract induced by the administration of anticancer agents.

However, in general, in the case of formulating a drug compound, the lower the content becomes, the more likely the drug compound suffers from a mutual action with drug additives, and therefore, the drug compound is worried about a lowering of its stability.

The 0.1 mg tablet of ramosetron hydrochloride as a product employs a packaging state into which a desiccant is incorporated. Accordingly, this product was a pharmaceutically stable formulation and did not have a problem as goods on the market. However, it is thought that in low-content formulations, a stabilizing effect is insufficient only by the desiccant.

[Patent Document 1] European Patent No. 381,422

DISCLOSURE OF THE INVENTION

Consequently, it is demanded to provide a stabilized formulation of ramosetron or a pharmaceutically acceptable salt thereof under a temperature/humidity condition, especially at a low content.

Though usual formulations of ramosetron and a pharmaceutically acceptable salt thereof including currently marketed ramosetron hydrochloride are found to slightly form decomposition products upon irradiation with light, they are stable under a temperature/humidity storage condition. The present inventors made investigations about formulations optimum to adaptation diseases for which an effect is expected at a low dose, such as irritable bowel syndrome and knew that when stored under a high-temperature and high-humidity condition, ramosetron or its pharmaceutically acceptable salt is lowered with respect to its quantitative value and is likely decomposed. Then, for the sake of developing formulations of ramosetron or its pharmaceutically acceptable salt that is stable even at a low content, the present inventors made extensive and intensive investigations. As a result, it has been found that ascorbic acid gives rise to a remarkable stabilizing effect against temperature/humidity. The present inventors further made investigations about the stabilizing effect by propyl gallate. As a result, it has been unexpectedly found that propyl gallate gives rise to a far remarkable stabilizing effect as compared with the stabilizing effect against temperature/humidity by enolic acids that give rise to an excellent stabilizing effect, such as ascorbic acid and erythorbic acid. The present inventors further made extensive and intensive investigations. As a result, it has been surprisingly found that hydroxycarboxylic acids or esters thereof such as citric acid (hydrate), citric acid (anhydride), tartaric acid, and carboxymethyl cellulose, aliphatic carboxylic acids or esters thereof, acidic amino acids, and carboxyl group-containing high-molecular substances such as carboxymethyl cellulose give rise to an extremely excellent stabilizing effect against temperature/humidity as compared with aromatic carboxylic acids or esters thereof such as propyl gallate described above.

Moreover, the present inventors have also found that in particular, when a coloring agent selected from the group consisting of yellow iron sesquioxide, red iron sesquioxide, and titanium oxide is added to ramosetron or its pharmaceutically acceptable salt, there gives rise to an extremely remarkable light stabilizing effect.

Specifically, this invention has been accomplished based on the foregoing findings and is to provide:

1. A stable oral solid drug composition of ramosetron or a pharmaceutically salt thereof, which is characterized by containing one or two or more members selected from the group consisting of an aliphatic carboxylic acid or an ester thereof, a hydroxycarboxylic acid or an ester thereof, an acidic amino acid, an enolic acid, an aromatic carboxyl compound or an ester thereof, and a carboxyl group-containing high-molecular substance;

2. A stable oral solid drug composition of ramosetron or a pharmaceutically salt thereof, which is characterized by containing one or two or more members selected from the group consisting of a hydroxycarboxylic acid or an ester thereof, an enolic acid, an aromatic carboxyl compound or an ester thereof, and a carboxyl group-containing high-molecular substance;

3. A stable oral solid drug composition of ramosetron or a pharmaceutically salt thereof, which is characterized by containing one or two or more members selected from the group consisting of a hydroxycarboxylic acid or an ester thereof and a carboxyl group-containing high-molecular substance;
4. The drug composition as set forth above in 1, wherein the aliphatic carboxylic acid or its ester is one or two or more members selected from the group consisting of maleic acid, malonic acid, succinic acid, and fumaric acid;
5. The drug composition as set forth above in 1, wherein the hydroxycarboxylic acid or its ester is one or two or more members selected from the group consisting of tartaric acid, malic acid, and citric acid;
6. The drug composition as set forth above in 1, wherein the hydroxycarboxylic acid or its ester is one or two or more members selected from the group consisting of tartaric acid and citric acid;
7. The drug composition as set forth above in 1, wherein the acidic amino acid is aspartic acid or glutamic acid;
8. The drug composition as set forth above in 1, wherein the enolic acid is ascorbic acid or erythorbic acid;
9. The drug composition as set forth above in 1, wherein the aromatic carboxyl compound or its ester is phthalic acid or propyl gallate;
10. The drug composition as set forth above in 1, wherein the carboxyl group-containing high-molecular substance is carboxymethyl cellulose or alginic acid;
11. The drug composition as set forth above in any one of 1 to 10, wherein the compounding amount of one or two or more members selected from the group consisting of an aliphatic carboxylic acid or an ester thereof, a hydroxycarboxylic acid or an ester thereof, an acidic amino acid, an enolic acid, an aromatic carboxyl compound or an ester thereof, and a carboxyl group-containing high-molecular substance is from 0.01 to 90% by weight in the preparation;
12. The drug composition as set forth above in any one of 1 to 11, wherein the compounding amount of ramosetron or its pharmaceutically acceptable salt is from 0.0001 to 0.5% by weight in the preparation;
13. The drug composition as set forth above in 12, wherein the compounding amount of ramosetron or its pharmaceutically acceptable salt is from 0.0005 to 0.05% by weight in the preparation;
14. The drug composition as set forth above in any one of 1 to 13, further containing a light stabilizer;
15. The drug composition as set forth above in 14, wherein the light stabilizer is one or two or more members selected from the group consisting of yellow iron sesquioxide, red iron sesquioxide, and titanium oxide;
16. A stabilization method of an oral solid drug composition of ramosetron or a pharmaceutically acceptable salt thereof, which is characterized by compounding one or two or more members selected from the group consisting of an aliphatic carboxylic acid or an ester thereof, a hydroxycarboxylic acid or an ester thereof, an acidic amino acid, an enolic acid, an aromatic carboxyl compound or an ester thereof, and a carboxyl group-containing high-molecular substance;
17. The stabilization method as set forth above in 16, wherein the aliphatic carboxylic acid or its ester is one or two or more members selected from the group consisting of maleic acid, malonic acid, succinic acid, and fumaric acid;
18. The stabilization method as set forth above in 16, wherein the hydroxycarboxylic acid or its ester is one or two or more members selected from the group consisting of tartaric acid, malic acid, and citric acid;
19. The stabilization method as set forth above in 16, wherein the acidic amino acid is aspartic acid or glutamic acid;
20. The stabilization method as set forth above in 16, wherein the enolic acid is ascorbic acid or erythorbic acid;
21. The stabilization method as set forth above in 16, wherein the aromatic carboxyl compound or its ester is phthalic acid or propyl gallate;
22. The stabilization method as set forth above in 16, wherein the carboxyl group-containing high-molecular substance is carboxymethyl cellulose or alginic acid;
23. The stabilization method as set forth above in any one of 16 to 22, wherein the compounding amount of one or two or more members selected from the group consisting of an aliphatic carboxylic acid or an ester thereof, a hydroxycarboxylic acid or an ester thereof, an acidic amino acid, an enolic acid, an aromatic carboxyl compound or an ester thereof, and a carboxyl group-containing high-molecular substance is from 0.01 to 90% by weight in the preparation;
24. The stabilization method as set forth above in any one of 16 to 23, wherein the compounding amount of ramosetron or its pharmaceutically acceptable salt is from 0.0001 to 0.5% by weight in the preparation;
25. The stabilization method as set forth above in 24, wherein the compounding amount of ramosetron or its pharmaceutically acceptable salt is from 0.0005 to 0.05% by weight in the preparation;
26. The stabilization method as set forth above in any one of 16 to 25, further compounding a light stabilizer; and
27. The stabilization method as set forth above in 26, wherein the light stabilizer is one or two or more members selected from the group consisting of yellow iron sesquioxide, red iron sesquioxide, and titanium oxide.

In general, it is considered that an antioxidant is classified into three categories in view of its mechanism of action. *Iyakuhin No Kaihatsu*, Volume 12, "Formulation Materials II", page 310, published on Oct. 28, 1990 enumerates (1) substances that are oxidized in place of a chemical that is weak to oxidation, to consume oxygen and protect the chemical (for example, water-soluble reducing agents such as ascorbic acid), (2) substances that are considered to react as a receptor of a free radical, to intercept chain reaction (for example, fat-soluble antioxidants such as propyl gallate), and (3) substances that do not have an anti-oxidant action alone but, when combined with an antioxidant, reinforce its antioxidant action (for example, synergists of fat-soluble antioxidants such as citric acid). The mechanism of stabilization of ramosetron or its pharmaceutically acceptable water has not been clarified in detail yet. However, in view of the fact that citric acid that does not substantially have an anti-oxidant action alone brought stable ramosetron formulations as compared with other antioxidants, it is estimated that the suppression of decomposition under a temperature/humidity storage condition is not made based on mere suppression of oxidative decomposition.

Incidentally, for the purpose of lowering vascular stimulation of injection preparations containing a serotonin receptor antagonist, there is disclosed an invention related to an injection preparation containing a specific serotonin antagonist and a polyhydric alcohol or a sugar alcohol and a citric acid salt and having a pH adjusted at from 3 to 5 (JP-A-7-10753). However, the subject invention is different from this invention with respect to the technical problems and neither describes nor suggests stable oral solid formulations at a low content of ramosetron hydrochloride against temperature/humidity.

Also, there is disclosed an invention related to a stable drug composition against racemization containing cilansetron as a 5-HT receptor antagonist, which is an optically active substance and is racemized in formulation, and a water-soluble acidic substance (JP-A-11-92369). However, this invention is different from the technology for suppressing the racemization with respect to the technical problems.

In addition, the present inventors carried out clinical tests against patients of diarrhea-predominant irritable bowel syndrome over 12 weeks using the foregoing stabilized formulation of low-content ramosetron hydrochloride. As a result, remarkable effectiveness has been confirmed, leading to accomplishment of this invention.

Specifically, this invention is concerned with:
28. A pharmaceutical composition for therapy of diarrhea-predominant irritable bowel syndrome, containing from 0.002 to 0.02 mg of ramosetron hydrochloride as a daily dose or an equivalent molar amount of ramosetron or its pharmaceutically acceptable other salt as an active ingredient; or
29. A pharmaceutical composition for improving diarrhea symptom of irritable bowel syndrome, containing from 0.002 to 0.02 mg of ramosetron hydrochloride as a daily dose or an equivalent molar amount of ramosetron or its pharmaceutically acceptable other salt as an active ingredient.

Also, this invention is concerned with:
30. Use of from 0.002 to 0.02 mg of ramosetron hydrochloride as a daily dose or an equivalent molar amount of ramosetron or its pharmaceutically acceptable other salt for the manufacture of a medicament for the treatment of diarrhea-predominant irritable bowel syndrome; or
31. Use of from 0.002 to 0.02 mg of ramosetron hydrochloride as a daily dose or an equivalent molar amount of ramosetron or its pharmaceutically acceptable other salt for the manufacture of a medicament for the improvement of diarrhea symptom of irritable bowel syndrome.

Also, this invention is concerned with:
32. A therapeutic method of diarrhea-predominant irritable bowel syndrome, including administering a patient with from 0.002 to 0.02 mg of ramosetron hydrochloride as a daily dose or an equivalent molar amount of ramosetron or its pharmaceutically acceptable other salt; or
33. An improving method of diarrhea symptom of irritable bowel syndrome, including administering a patient with from 0.002 to 0.02 mg of ramosetron hydrochloride as a daily dose or an equivalent molar amount of ramosetron or its pharmaceutically acceptable other salt.

The dosage of ramosetron hydrochloride exhibited by the clinical test results in Test Example 2 described later is 0.005 mg and 0.01 mg for oral administration once a day. However, in view of the fact that the administration of 0.005 mg revealed a remarkable therapeutic effect comparable to that in the administration of 0.01 mg, effectiveness can be further expected even in an approximately half amount. Also, the subject of Test Example 2 is the Japanese adult patients, possibility that the optimum dose to children is further small is suggested, and the optimum dose to Europeans and Americans may often be twice that to Japanese. Accordingly, though the dosage of ramosetron hydrochloride is especially preferably in the range of from 0.002 to 0.02 mg per day, it is thought that it is possible to improve diarrhea-predominant irritable bowel syndrome or diarrhea symptom of irritable bowel syndrome at a dose falling within the range of from 0.001 to 0.05 mg per day depending upon the age or racial difference of a patient.

The oral drug composition of this invention will be described below.

Ramosetron to be used in this invention is a drug compound having the foregoing chemical name and described in Example 44, etc. of JP-B-6-25153, and specific examples of its pharmaceutically acceptable salts include salts of mineral acids such as hydrochloric acid, sulfuric acid, phosphoric acid, and hydrobromic acid; salts of organic acids such as acetic acid, oxalic acid, succinic acid, citric acid, maleic acid, malic acid, fumaric acid, tartaric acid, and methanesulfonic acid; and salts of acidic amino acid such as glutamic acid and aspartic acid. Of these, marketed ramosetron hydrochloride is preferable. Also, ramosetron or its pharmaceutically acceptable salt can be easily obtained according to the production process described in the above-cited patent document.

The amount of ramosetron or its pharmaceutically acceptable salt to be used is not particularly limited so far as it is an effective amount. In particular, though it was found that ramosetron or its pharmaceutically acceptable salt is unstable against temperature/humidity in low-dose formulations, it is estimated that this matter is a substantially inherent problem even in high-dose formulations, and therefore, a similar stabilizing effect can be expected. Accordingly, the use amount thereof is not limited to an effective amount against adaptation diseases of irritable bowel syndrome but includes effective amounts of the conventional goods on the market. Concretely, the amount of ramosetron or its pharmaceutically acceptable salt to be compounded is preferably from 0.0001 to 0.5 mg, more preferably from 0.0001 to 0.25% by weight, and further preferably from 0.0005 to 0.05% by weight in the preparation. Also, when the amount of ramosetron or its pharmaceutically acceptable salt to be used is expressed in terms of unit formulation, it is specifically from 0.1 to 500 μg, more preferably from 0.1 to 250 μg, and further preferably from 1 to 50 μg.

The compound for stabilizing ramosetron, which is used in this invention, is a specific compound having a carbonyl group as described previously and stabilizes ramosetron or its pharmaceutically acceptable salt. Specific examples of the specific compound having a carbonyl group include aliphatic carboxylic acids (in detail, saturated or unsaturated, linear or branched aliphatic mono-, di- or tri-carboxylic acids, and especially aliphatic carboxylic acids having from 3 to 36 carbon atoms) or esters thereof, hydroxycarboxylic acids (in detail, saturated or unsaturated, linear or branched aliphatic hydroxymono-, di- or tri-carboxylic acids, and especially hydroxycarboxylic acids having from 3 to 36 carbon atoms) or esters thereof, acidic amino acids, enolic acids, aromatic carboxyl compounds (in detail, aromatic mono-, di- or tri-carboxylic acids that may be substituted with an alkyl group having from 1 to 4 carbon atoms or a hydroxyl group, and especially aromatic carboxylic acids having from 7 to 20 carbon atoms) or esters thereof, and carboxyl group-containing high-molecular substances. These compounds can be properly used singly or in combinations of two or more thereof.

Above all, as the specific compound having a carbonyl group, hydroxycarboxylic acids or esters thereof, carboxyl group-containing high-molecular substances, aromatic carboxyl compounds or esters thereof, and enolic acids are preferable; especially, hydroxycarboxylic acids or esters thereof, carboxyl group-containing high-molecular substances, and aromatic carboxyl compounds or esters thereof are preferable; and optimally, hydroxycarboxylic acids or esters thereof and carboxyl group-containing high-molecular substances are further preferable.

As the aliphatic carboxylic acids, maleic acid, malonic acid, succinic acid, and fumaric acid are preferable. As the hydroxycarboxylic acids, tartaric acid, malic acid, and citric acid are preferable, with tartaric acid and citric acid being further preferable. As the acidic amino acids, glutamic acid and aspartic acid are preferable. As the aromatic carboxyl compounds, phthalic acid and propyl gallate are preferable, with propyl gallate being further preferable. As the carboxyl group-containing high-molecular substances, carboxymethyl cellulose and alginic acid are preferable, with carboxymethyl cellulose being further preferable. Also, as the enolic acids, ascorbic acid and erythorbic acid are preferable, with ascorbic acid being further preferable.

With respect to the foregoing carbonyl compound, it is clarified that hydrates or anhydrides free from water of crystallization, such as citric acid hydrate or citric anhydride, also exhibit the stabilizing effect of this invention, and all of hydrates, anhydrides, or mixtures thereof are included. Also, though the high-molecular substances are not particularly limited with respect to the degree of polymerization and molecular weight, in the case of carboxymethyl cellulose, the weight average molecular weight is especially preferably about 110,000, and in the case of alginic acid, the weight average molecular weight is especially preferably about 200,000.

The compounding amount of the compound that stabilizes ramosetron or its pharmaceutically acceptable salt is not limited so far as it is an amount at which the compound stabilizes ramosetron or its pharmaceutically acceptable salt (preferably ramosetron hydrochloride). The compounding amount is from 0.01 to 90% by weight, and preferably from 0.01 to 50% by weight in the preparation, and in view of the productivity, it is further preferably from 0.1 to 10% by weight.

Various drug additives are properly used in the oral solid drug composition of this invention to prepare a formulation. Such drug additives are not particularly limited so far as they are pharmaceutically acceptable additives. Examples thereof include excipients, binders, disintegrating agents, sour agents, blowing agents, artificial sweeteners, flavors, lubricants, and coloring agents. Examples of excipients include lactose, crystalline cellulose, microcrystalline cellulose, D-sorbitol, and D-mannitol. Examples of binders include hydroxypropylmethyl cellulose, hydroxypropyl cellulose, povidone, polyvinyl alcohol, methyl cellulose, and gum arabic. Examples of disintegrating agents include cornstarch, potato starch, carmellose, carmellose calcium, carmellose sodium, crosscarmellose sodium, low-substitution degree hydroxypropyl cellulose, and crosspovidone. Examples of sour agents include citric acid, tartaric acid, and malic acid. Examples of blowing agents include sodium bicarbonate. Examples of artificial sweeteners include saccharin sodium, glycyrrhizin dipotassium, aspartame, stevia, and thaumatin. Examples of flavors include lemon, lemon lime, orange, and menthol. Examples of lubricants include magnesium stearate, calcium stearate, sucrose fatty acid esters, polyethylene glycol, talc, and stearic acid. Incidentally, as the coloring agents, for example, yellow iron sesquioxide, red iron sesquioxide, titanium oxide, Food Yellow No. 4 and No. 5, Food Red No. 3 and No. 102, and Food Blue No 3 can be used. Especially, it is confirmed that when yellow iron sesquioxide, red iron sesquioxide, or titanium oxide is compounded, there gives rises a remarkable light stabilizing effect, and these coloring agents also act as a light stabilizer. The drug additives can be properly added in an adequate amount singly or in combinations of two or more thereof.

The drug composition of this invention can be produced by a method that is known itself and can be formed into, for example, a powder, a tablet, a film-coated tablet, a disintegrable tablet in oral cavity, or the like. With respect to disintegrable tablets in oral cavity, a lot of technologies are developed, and there are no particular limitations. For example, the drug composition of this invention can be formed into a disintegrable tablet in oral cavity according to U.S. Pat. No. 5,466,464, U.S. Pat. No. 5,576,014, U.S. Pat. No. 6,589,554, WO 03/009831, and WO 02/082057.

As the method of adding a coloring agent, in addition to film coating, in the case where film coating is difficult as in quick disintegrable tablets in oral cavity, there are enumerated production processes by performing wet granulation as a binding liquid containing ramosetron or its pharmaceutically acceptable salt and a part or the whole of a coloring agent at the time of granulation, or wet granulation of a coloring agent-containing powder with a binding liquid containing ramosetron or its pharmaceutically acceptable salt. The addition amount of the coloring agent is adequately determined according to the kind of the coloring agent or the addition method. For example, in the case of film coating, the addition amount of the coloring agent is usually from 0.01 to 10% by weight, and preferably from 0.05 to 2% by weight based on the whole of the composition. In the case of performing wet granulation as a binding liquid containing ramosetron or its pharmaceutically acceptable salt and a part or the whole of a coloring matter at the time of granulation, or wet granulation of a coloring matter-containing powder with a binding liquid containing ramosetron or its pharmaceutically acceptable salt, the addition amount of the coloring agent is usually from 0.1 to 20% by weight, and preferably from 0.2 to 10% by weight based on the whole of the composition, and in view of the productivity, it is further preferably from 0.2 to 5% by weight. For example, the process comprises a step of dissolving or suspending ramosetron or its pharmaceutically acceptable salt and optionally, an organic acid and a coloring agent in purified water and a step of spraying the subject aqueous solution or suspension into a powder having an excipient and optionally, an organic acid and a coloring agent compounded therein in a wet granulator such as a fluidized bed granulator and then drying. Pharmaceutically acceptable drug additives may be uniformly dispersed in and added to the subject aqueous solution or suspension and/or powder to be fluidized. The subject aqueous solution or suspension can be used in a concentration as a binder to be employed in the usual wet granulation.

The stabilization of the oral solid drug composition of ramosetron or its pharmaceutically acceptable salt of this invention can be carried out by the method described above in the description of the invention regarding the drug composition.

BEST MODE FOR CARRYING OUT THE INVENTION

This invention will be further described below with reference to the following Examples, Comparative Examples and Test Examples, but it should not be construed that this invention is limited to these Examples. Incidentally, the term "part" shown below refers to a part by weight.

Comparative Example 1

| | |
|---|---|
| Ramosetron: | 0.02 parts |
| Lactose: | 86 parts |
| Hydroxypropyl cellulose: | 3 parts |
| Yellow iron sesquioxide: | 0.2 parts |
| Titanium oxide: | 10 parts |
| Light silicic anhydride: | 0.3 parts |

Three parts of hydroxypropyl cellulose and 0.02 parts of ramosetron hydrochloride were dissolved in 35 parts of water with stirring using a magnetic stirrer, with which were then kneaded 10 parts of titanium oxide and 0.2 parts of yellow iron sesquioxide using a triturator, to prepare a spray liquid (hydroxypropyl cellulose, concentration: 8% by weight). Next, 86 parts of lactose was charged in a fluidized bed granulator (a product name: FLOW COATER, manufactured by Freund Corporation), and the foregoing spray liquid was sprayed at a spray rate of 5 g/min to perform fluidizing granulation. After the granulation, the granulated material was dried at an intake air temperature of 40° C. for 5 minutes, and 0.3 parts of light silicic anhydride was then mixed to obtain a comparative powder of the formulation of this invention.

Example 1

| | |
|---|---|
| Ramosetron hydrochloride | 0.02 part |
| Lactose | 86 parts |
| Hydroxypropyl cellulose | 3 parts |
| Tartaric acid | 1 part |
| Yellow iron sesquioxide | 0.2 part |
| Titanium oxide | 10 parts |
| Light silicic acid anhydride | 0.3 part |

Hydroxypropyl cellulose (3 parts), 0.02 part of ramosetron hydrochloride and 1 part of tartaric acid were dissolved in 35 parts of water with stirring using a magnetic stirrer and kneaded with 10 parts of titanium oxide and 0.2 part of yellow iron sesquioxide using a grinding machine, and a spraying liquid (hydroxypropyl cellulose concentration: 8% by weight) was prepared. After that, 86 parts of lactose were charged in a fluid layer granulator (Flow Coater; manufactured by Freund) and the above spraying liquid was sprayed at a spraying rate of 5 g/minute to conduct a fluid granulation. The granules were dried for 5 minutes at an intake air temperature of 40° C. and then mixed with 0.3 part of light silicic acid anhydride to give a diluted powder preparation.

Example 2

| | |
|---|---|
| Ramosetron hydrochloride | 0.0008 part |
| Mannitol | 89 parts |
| Citric acid anhydride | 0.1 part |
| Maltose | 10 part |
| Red iron sesquioxide | 1 part |
| Magnesium stearate | 1 part |

Maltose (10 parts), 0.0008 part of ramosetron hydrochloride, 0.1 part of citric acid anhydride and 1 part of red iron sesquioxide were suspended in 67 parts of water with stirring using a magnetic stirrer to prepare a spraying liquid (concentration: 15% by weight). After that, 89 parts of mannitol were charged in a fluidized bed granulator (Flow Coater; manufactured by Freund) and the above spraying liquid was sprayed at a spraying rate of 10 g/minute to conduct a fluid granulation. After the granulation, the granules were dried for 5 minutes at an intake air temperature of 40° C. and then mixed with 1 part of magnesium stearate. The mixed powder was made into tablets using a rotary tableting machine at the rate of 120 mg per tablet to give tablets having about 1 kp of initial hardness. They were preserved for 18 hours at a relative humidity of 75% and then preserved for 4 hours at a relative humidity of 40% to give intraorally disintegrating tablets.

Example 3

The same manufacturing method as in Example 2 was conducted except that the adding amount of citric acid anhydride was changed to 0.2 part to give intraorally disintegrating tablets.

Example 4

The same manufacturing method as in Example 2 was conducted except that the adding amount of citric acid anhydride was changed to 0.5 part to give intraorally disintegrating tablets.

Example 5

| | |
|---|---|
| Ramosetron hydrochloride | 0.0008 part |
| Mannitol | 89 parts |
| Ascorbic acid | 0.2 part |
| Maltose | 10 parts |
| Red iron sesquioxide | 1 part |
| Magnesium stearate | 1 part |

Maltose (10 parts), 0.0008 part of ramosetron hydrochloride, 0.2 part of ascorbic acid and 1 part of red iron sesquioxide were suspended in 67 parts of water with stirring using a magnetic stirrer and a spraying liquid (concentration: 15% by weight) was prepared. After that, 89 parts of mannitol were charged in a fluidized bed granulator (Flow Coater; manufactured by Freund) and the above spraying liquid was sprayed at a spraying rate of 10 g/minute to conduct a fluid granulation. After the granulation, the granules were dried for 5 minutes at an intake air temperature of 40° C. and then mixed with 1 part of magnesium stearate. The mixed powder was made into tablets using a rotary tableting machine at the rate of 120 mg per tablet to give tablets having about 1 kp of initial hardness. They were preserved at 25° C. for 18 hours at a relative humidity of 75% and then preserved at 30° C. for 4 hours at a relative humidity of 40% to give intraorally disintegrating tablets.

Example 6

The same manufacturing method as in Example 5 was conducted except that the adding amount of ascorbic acid was changed to 0.5 part to give intraorally disintegrating tablets.

Example 7

| | |
|---|---|
| Ramosetron hydrochloride | 0.0008 part |
| Mannitol | 88 parts |
| Maltose | 10 parts |
| Yellow iron sesquioxide | 1 part |
| Citric acid anhydride | 0.2 part |
| Magnesium stearate | 1 part |

Maltose (10 parts), 0.0008 part of ramosetron hydrochloride, 1 part of red iron sesquioxide and 0.2 part of citric acid anhydride were suspended in 67 parts of water with stirring using a magnetic stirrer and a spraying liquid (concentration:

15% by weight) was prepared. After that, 88 parts of mannitol were charged in a fluidized bed granulator (Flow Coater; manufactured by Freund) and the above spraying liquid was sprayed at an intake air temperature of 50° C., a spraying rate of 10 g/minute and a cycle of spray/dry/shaking of 15 seconds/15 seconds/10 seconds to conduct a fluid granulation. After the granulation, the granules were dried for 5 minutes at an intake air temperature of 40° C. and then mixed with 1 part of magnesium stearate. The mixed powder was made into tablets using a rotary tableting machine at the rate of 120 mg per tablet to give tablets having about 1 kp of initial hardness. They were preserved at 25° C. for 18 hours at a relative humidity of 75% and then preserved at 30° C. for 4 hours at a relative humidity of 40% to give intraorally disintegrating tablets.

Example 8

| Ramosetron hydrochloride | 0.01 part |
| Avicel | 86 parts |
| Low substituted hydroxypropyl cellulose | 10 parts |
| Citric acid anhydride | 0.5 part |
| Hydroxypropyl cellulose | 3 parts |
| Magnesium stearate | 0.5 part |

Hydroxypropyl cellulose (3 parts), 0.5 part of citric acid anhydride and 0.01 part of ramosetron hydrochloride were dissolved in 27 parts of water with stirring using a magnetic stirrer to prepare a spraying liquid (concentration of hydroxypropyl cellulose: 10% by weight). After that, 86 parts of Avicel and 10 parts of low-substituted hydroxypropyl cellulose were charged in a fluidized bed granulator (trade name: GPCG-5 manufactured by Powlex) and the above spraying liquid was sprayed at a spraying rate of 100 g/minute to conduct a fluid granulation. After the granulation, the granules were dried at 40° C. for 5 minutes and then mixed with 0.5 g of magnesium stearate. The mixed powder was made into tablets using a rotary tableting machine at the rate of 100 mg per tablet to give tablets.

Example 9

| Ramosetron hydrochloride | 0.1 part |
| Lactose | 77 parts |
| Corn starch | 19 parts |
| Carboxymethyl cellulose (CMC) | 5 parts |
| Hydroxypropyl cellulose | 3 parts |
| Magnesium stearate | 0.3 part |

Hydroxypropyl cellulose (3 parts) and 0.1 part of ramosetron hydrochloride were dissolved in 35 parts of water with stirring using a magnetic stirrer to prepare a spraying liquid (concentration of hydroxypropyl cellulose: 8% by weight). After that, 77 parts of lactose, 19 parts of corn starch and 5 parts of CMC were charged in a fluidized bed granulator (trade name: Flow Coater manufactured by Freund) and the above spraying liquid was sprayed at a spraying rate of 10 g/minute to conduct a fluid granulation. After the granulation, the granules were dried at 5 minutes at an intake air temperature of 40° C. and then mixed with 0.3 parts of magnesium stearate. The mixed powder was made into tablets using a rotary tableting machine at the rate of 120 mg per tablet to give tablets.

Example 10

| Ramosetron hydrochloride | 0.0008 part |
| Mannitol | 89 parts |
| Propyl gallate | 5 parts |
| Maltose | 10 parts |
| Magnesium stearate | 1 part |

Maltose (10 parts), 0.0008 part of ramosetron hydrochloride and 5 parts of propyl gallate were dissolved in 67 parts of water with stirring using a magnetic stirrer to prepare a spraying liquid (concentration: 15% by weight). After that, 89 parts of mannitol were charged in a fluidized bed granulator (Flow Coater manufactured by Freund) and the above spraying liquid was sprayed to conduct a fluid granulation. After the granulation, the granules were dried at 5 minutes at an intake air temperature of 40° C. and then mixed with 1 part of magnesium stearate. The mixed powder was made into tablets using a rotary tableting machine at the rate of 120 mg per tablet to give tablets.

[Evaluation of Stability]

Test Example 1

Evaluation of Stability of Ramosetron Hydrochloride Under Various Storage Conditions Test Method The stabilizing effect of the formulation of this invention was evaluated by storing the formulation of this invention under various storage conditions (under opening of bottle at 25° C. and 75% RH, under opening of bottle at 40° C. and 75% RH, under sealing of bottle at 25° C. and 60% RH, under sealing of bottle at 40° C. and 75% RH, or under irradiation with cool white fluorescent lamp of 1,000 Lux) and after passing for a fixed period of time, calculating a quantitative value of the stored product under various conditions against the quantitative value of the stored product at 5° C. according to the formulation of this invention. The quantitative determination was carried out by the liquid chromatography.

<Results and Consideration>

With respect to a 0.02% powder of ramosetron hydrochloride not containing a specific compound having a carbonyl group and a 0.02% powder of ramosetron hydrochloride containing a specific compound having a carbonyl group such as a citric anhydride, the stability of ramosetron hydrochloride in each of the formulations under a temperature/humidity condition was evaluated. The results thus obtained are shown in Table 1.

TABLE 1

| Storage condition and storage period of time | Quantitative value (%) | |
| --- | --- | --- |
| | Comparative Example 1 | Example 1 |
| Under opening of bottle at 25° C. and 75% RH for 2 months | 86 | 98 |
| Under opening of bottle at 40° C. and 75% RH for 2 months | 64 | 95 |

TABLE 1-continued

| | Quantitative value (%) | |
|---|---|---|
| Storage condition and storage period of time | Comparative Example 1 | Example 1 |
| Under sealing of bottle at 40° C. and 75% RH for 2 months | 75 | 97 |

In the 0.02% powder of ramosetron hydrochloride not containing a specific compound having a carbonyl group according to Comparative Example 1, a lowering of the quantitative value was found. In contrast, in the powder containing tartaric acid according to Example 1, a change of the quantitative value was not substantially found as compared with the stored product at 5° C. From these results, it has become clear that by adding tartaric acid to ramosetron hydrochloride, a remarkable stabilizing effect of ramosetron hydrochloride against the temperature/humidity is found.

Incidentally, in the case where a desiccant was put into Comparative Example 1, and the powder was stored under the same condition, a change of the quantitative value was not substantially found. In formulations having a high content of ramosetron, a countermeasure using a desiccant may be considered as in marketed products, but it is possible to similarly stabilize a formulation itself by containing a specific compound having a carbonyl group.

Subsequently, with respect to a 1 μg tablet of ramosetron hydrochloride not containing a specific compound having a carbonyl group and a 1 μg tablet of ramosetron hydrochloride containing a specific compound having a carbonyl group, such as ascorbic acid or citric anhydride, the stability of ramosetron hydrochloride in each of the formulations under a temperature/humidity condition was evaluated. The results thus obtained are shown in Table 2.

TABLE 2

| Storage condition and storage period of time | Quantitative value (%) | | | | | |
|---|---|---|---|---|---|---|
| | Comparative Example 2 | Example 2 | Example 3 | Example 4 | Example 5 | Example 6 |
| Under sealing of bottle at 40 ° C. and 75% RH for one moth | 33 | 96 | 97 | 97 | 54 | 62 |

In the 1 μg tablet of ramosetron hydrochloride not containing a specific compound having a carbonyl group according to Comparative Example 2, since the content of ramosetron hydrochloride is small as compared with that in Comparative Example 1, a large lowering of the quantitative value was found. In contrast, in the citric anhydride-containing tablets having a small content of ramosetron hydrochloride similarly according to Examples 2, 3 and 4, a change of the quantitative value was not substantially found as compared with the stored product at 5° C. Also, in the ascorbic acid-containing tablets according to Examples 5 and 6, an improving effect of ramosetron hydrochloride against the temperature/humidity was found as compared with Comparative Example 2. From these results, it has become clear that by adding ascorbic acid or citric anhydride to ramosetron hydrochloride, a stabilizing effect of ramosetron hydrochloride against the temperature/humidity is found and that the stabilizing effect by citric anhydride is larger than that by ascorbic acid.

Also, it has been noted from Tables 1 and 2 that the specific compound having a carbonyl group contributes to the stabilization of a formulation regardless of the content of ramosetron to be contained in the formulation.

With respect to a 1 μg tablet of ramosetron hydrochloride not containing a specific compound having a carbonyl group and not containing red iron sesquioxide or yellow iron sesquioxide and a 1 μg tablet of ramosetron hydrochloride containing a specific compound having a carbonyl group such as a citric anhydride and containing red iron sesquioxide or yellow iron sesquioxide, the stability of ramosetron hydrochloride in each of the formulations under a temperature/humidity condition was evaluated. The results thus obtained are shown in Table 3.

TABLE 3

| | Quantitative value (%) | | |
|---|---|---|---|
| Storage condition and storage period of time | Comparative Example 2 | Example 3 | Example 7 |
| Under opening of bottle at 25° C. and 75% RH for one month | 68 | 101 | 99 |
| Under sealing of bottle at 40° C. and 75% RH for one month | 33 | 97 | 98 |
| Under irradiation with 1,000 Lux for one month | 0 | 93 | 94 |

First of all, against the temperature/humidity, in the 1 μg tablet of ramosetron hydrochloride not containing a specific compound having a carbonyl group according to Comparative Example 2, a lowering of the quantitative value was found. In contrast, in the citric anhydride-containing tablets according to Examples 3 and 7, a change of the quantitative value was not substantially found as compared with the stored product at 5° C. Next, against the light, in the 1 μg tablet of ramosetron hydrochloride not containing yellow iron sesquioxide according to Comparative Example 2, the existence of ramosetron hydrochloride was not found. In contrast, in the 1 μg tablet of ramosetron hydrochloride containing red iron sesquioxide according to Example 3 and the 1 μg tablet of ramosetron hydrochloride containing yellow iron sesquioxide according to Example 7, a change of the quantitative value was not substantially found as compared with the stored product at 5° C. From these results, it has become clear that by adding citric anhydride and red iron sesquioxide or yellow iron sesquioxide to ramosetron hydrochloride, a stabilizing effect of ramosetron hydrochloride against the temperature/humidity and the light is found.

With respect to a 10 μg tablet of ramosetron hydrochloride containing a specific compound having a carbonyl group, the stability of ramosetron hydrochloride in the formulation of this invention was evaluated under a temperature/humidity condition. The results thus obtained are shown in Table 4.

TABLE 4

| Storage condition and storage period of time | Quantitative value (%) Example 8 |
|---|---|
| Under sealing of bottle at 25° C. and 60% RH for 6 months | 100 |
| Under sealing of bottle at 40° C. and 75% RH for 6 months | 99 |

In the tablet containing citric acid hydrate according to Example 8, a change of the quantitative value was not substantially found as compared with the stored product at 5° C. From these results, it has become clear that even by adding citric acid hydrate to ramosetron hydrochloride in place of the citric anhydride, a remarkable stabilizing effect of ramosetron hydrochloride against the temperature/humidity is found.

With respect to a 100 μg tablet of ramosetron hydrochloride containing a specific compound having a carbonyl group, the stability of ramosetron hydrochloride in the formulation of this invention was evaluated under a temperature/humidity condition. The results thus obtained are shown in Table 5.

TABLE 5

| Storage condition and storage period of time | Quantitative value (%) Example 9 |
|---|---|
| Under opening of bottle at 25° C. and 75% RH for 4 months | 100 |
| Under opening of bottle at 40° C. and 75% RH for 4 months | 99 |

In the tablet containing CMC according to Example 9, a change of the quantitative value was not substantially found as compared with the stored product at 5° C. From these results, it has become clear that even by adding CMC to ramosetron hydrochloride in place of the citric anhydride or citric acid hydrate, a remarkable stabilizing effect of ramosetron hydrochloride against the temperature/humidity is found.

With respect to a 1 μg tablet of ramosetron hydrochloride containing propyl gallate, the stability of ramosetron hydrochloride in the formulation of this invention was evaluated under a temperature/humidity condition. The results thus obtained are shown in Table 6.

TABLE 6

| Storage condition and storage period of time | Quantitative value (%) | |
|---|---|---|
| | Comparative Example 2 | Example 10 |
| Under sealing of bottle at 40° C. and 75% RH for one month | 33 | 87 |

In the 1 μg tablet of ramosetron hydrochloride containing propyl gallate according to Example 10, a stabilizing effect was found in terms of the quantitative value as compared with the 1 μg tablet of ramosetron hydrochloride not containing a specific compound having a carbonyl group according to Comparative Example 2.

[Evaluation of Efficacy]

Test Example 2

Clinical Test to Patients Suffering from Diarrhea-Predominant Irritable Bowel Syndrome Clinical test was carried out under the following condition using male and female patients suffering from diarrhea-predominant irritable bowel syndrome (IBS) as subjects.

Subjects: Patients suffering from diarrhea-predominant IBS in accordance with the Rome II Diagnosis Standard (D. A. Drossman, et al., pages 351 to 432, Degnon Associates, McLean, 2000). Case Number: 418 cases Clinical Samples and Administration Methods: Placebo and ramosetron hydrochloride were orally administered for 12 weeks at 0.005 mg or 0.01 mg once daily.

Test Periods: Observation period for one week and treating period for 12 weeks

Observed Items:

1. Main Evaluated Items (1) General Improvement Effect for IBS Symptom (Evaluation by the Subjects)

After transition to the treating period, the starting date for administration of the clinical sample was defined as the first day. Every week, general improvement effect for IBS symptom by the clinical sample was evaluated taking all symptoms by IBS of the subjects into consideration, comparing with their state in the observation period, and this evaluation was recorded in a patient diary. Incidentally, scores for the general improvement effect for IBS symptom were as follows.

0=symptom disappeared
1=considerably improved
2=somewhat improved
3=unchanged
4=worsened The subjects where the score was 0 or 1 for two weeks or more during the four weeks were made monthly responders and the monthly responder rate per month was calculated separately for each group of 0.005 mg and 0.01 mg of placebo and ramosetron hydrochloride.

2. Subsidiary Evaluation Items (1) Improvement Effect for Gastralgia and Abdominal Discomfort (Evaluation by the Subjects)

After transition to the treating period, the starting date for administration of the clinical sample was defined as the first day. Every week, improvement effect on gastralgia and abdominal discomfort by the clinical sample was evaluated with the state in the observation period and was recorded in a patient diary. Incidentally, scores for the improvement effect for gastralgia and abdominal discomfort were as follows.

0=symptom disappeared
1=considerably improved
2=somewhat improved
3=unchanged
4=worsened (2) Improvement Effect for Bowel Movement (Evaluation by the Subjects)

After transition to the treating period, the starting date for administration of the clinical sample was defined as the first day. Every week, improvement effect on bowel movement by the clinical sample was evaluated comparing with the state in the observation period, and was recorded in a patient diary. Incidentally, scores for the improvement effect for bowel movement were as follows.

0=nearly normal state resulted
1=considerably improved
2=somewhat improved
3=unchanged
4=worsened (3) Degree of Seriousness of Gastralgia and Abdominal Discomfort During the periods of clinical test (both observation period and treating period), the subjects evaluated the degree of seriousness of gastralgia and abdominal discomfort for each day and wrote in a patient diary. Scores for the degree of seriousness of gastralgia and abdominal discomfort were as follows.

0=not noted
1=weak
2=medium
3=strong
4=very strong

(4) Shape of Feces (Property)

During the periods of clinical test, the subjects wrote the shape of feces (property) for each day using a score (type) of Bristol's feces shape scale in a patient diary. When there were plural defecations within a day or when different feces shapes (properties) were noted in one defecation, only one shape (property) which was the most representative one on that day (or for which the subject felt most troublesome) was written.

(5) Frequency of Defecation

During the periods of clinical test, the subjects wrote the frequency of defecations for each day in a patient diary.

(6) Pressure Feeling for a Defecation

During the periods of clinical test, the subjects wrote whether there was pressure feeling for a defecation for each day in a patient diary.

(7) Sensation of Residual Feces

During the periods of clinical test, the subjects wrote whether there was sensation of residual feces for each day in a patient diary.

With regard to (1) to (3) for the subsidiary evaluation items, they were also subjected to calculations of monthly responder rate the same as those for the main evaluation items. Results:

With regard to the final monthly responder date in the general improvement effect for the IBS symptom, it was 26.9% in a placebo group. On the other hand, in the groups of 0.005 mg and 0.01 mg of ramosetron hydrochloride, the monthly responder rates were 42.6% and 43.0%, respectively and were more than 15% than the responder rate in the placebo group. The p values for the groups of 0.005 mg and 0.01 mg to the placebo group were 0.0273 and 0.0264, respectively. With regard to the final monthly responder rates in the improvement effect for gastralgia and abdominal discomfort and in the improvement effect for state of defecation, the ramosetron hydrochloride group of 0.005 mg and 0.01 mg was also better than the placebo group to an extent of more than 10%.

From the above, the therapeutic effect of 0.005 mg and 0.01 mg of ramosetron hydrochloride to patients suffering from diarrhea-predominant irritable bowel syndrome was confirmed.

INDUSTRIAL APPLICABILITY

The oral solid drug composition of this invention can provide a stable formulation of ramosetron or a pharmaceutically acceptable salt thereof under a temperature/humidity condition, especially at a low content.

Also, it is possible to provide a clinically effective and excellent therapeutic agent of diarrhea-predominant irritable bowel syndrome or improving agent of diarrhea symptom of irritable bowel syndrome.

All documents mentioned herein are incorporated herein by reference in their entirety.

The invention claimed is:

1. A stable oral solid drug composition in solid dosage form comprising:
    ramosetron or a pharmaceutically acceptable salt thereof; and more than one member selected from the group consisting of following (i) to (vii):
        (i) an aliphatic carboxylic acid consisting of maleic acid, malonic acid, succinic acid, and fumaric acid, or an ester thereof;
        (ii) a hydroxycarboxylic acid consisting of tartaric acid, maleic acid, and citric acid or an ester thereof;
        (iii) an acidic amino acid consisting of aspartic acid or glutamic acid;
        (iv) an enolic acid consisting of ascorbic acid or erythorbic acid;
        (v) an aromatic carboxyl compound consisting of phthalic acid or propyl gallate or an ester thereof; and
        (vi) a carboxyl group-containing high-molecular substance consisting of carboxymethyl cellulose or alginic acid,
        (vii) one or more additives selected from the group consisting of excipients, binders, disintegrating agents, sour agents, blowing agents, artificial sweeteners, flavors, lubricants and coloring agents,
    wherein tartaric acid, maleic acid, or citric acid, or an ester thereof, is present in the composition;
    the one more members (i) to (vi) are present in an amount of 0.01 to 90 percent by weight based on total weight of the composition; and
    ramosetron or its pharmaceutically acceptable salt is present in an amount of 0.002 to 0.02 mg based on total weight of the composition.

2. A stable oral solid drug composition in solid dosage form comprising:
    ramosetron or a pharmaceutically acceptable salt thereof; and more than one member selected from the group consisting of following (i) to (v):
        (i) a hydroxycarboxylic acid consisting of tartaric acid, maleic acid, and citric acid or an ester thereof;
        (ii) an enolic acid consisting of ascorbic acid or erythorbic acid;
        (iii) an aromatic carboxyl compound consisting of phthalic acid or propyl gallate or an ester thereof; and
        (iv) a carboxyl group-containing high-molecular substance consisting of carboxymethyl cellulose or alginic acid,
        (v) one or more additives selected from the group consisting of excipients, binders, disintegrating agents, sour agents, blowing agents, artificial sweeteners, flavors, lubricants and coloring agents,
    wherein tartaric acid, maleic acid, or citric acid, or an ester thereof, is present in the composition
    the one more members (i) to (iv) are present in an amount of 0.01 to 90 percent by weight based on total weight of the composition; and
    ramosetron or its pharmaceutically acceptable salt is present in an amount of 0.002 to 0.02 mg based on total weight of the composition.

3. A method for making a stabilized oral solid drug composition of ramosetron or a pharmaceutically acceptable salt thereof, in solid dosage form comprising:
    compounding (a) ramosetron or its pharmaceutically acceptable salt and (b) more than one member selected from the group consisting of following (i) to (vii):
        (i) an aliphatic carboxylic acid consisting of maleic acid, malonic acid, succinic acid, and fumaric acid, or an ester thereof;
        (ii) a hydroxycarboxylic acid consisting of tartaric acid, maleic acid, and citric acid or an ester thereof;
        (iii) an acidic amino acid consisting of aspartic acid or glutamic acid;
        (iv) an enolic acid consisting of ascorbic acid or erythorbic acid;
        (v) an aromatic carboxyl compound consisting of phthalic acid or propyl gallate or an ester thereof; and
        (vi) a carboxyl group-containing high-molecular substance consisting of carboxymethyl cellulose or alginic acid,
        (vii) one or more additives selected from the group consisting of excipients, binders, disintegrating agents, sour agents, blowing agents, artificial sweeteners, flavors, lubricants and coloring agents, wherein tartaric acid, maleic acid, or citric acid, or an ester thereof, is compounded;

the one more members (i) to (vi) are present in an amount of 0.01 to 90 percent by weight based on total weight of the composition; and ramosetron or its pharmaceutically acceptable salt is present in an amount of 0.002 to 0.02 mg based on total weight of the composition.

4. A method for making a stabilized oral solid drug composition of ramosetron or a pharmaceutically acceptable salt thereof, in solid dosage form comprising:

compounding (a) ramosetron or its pharmaceutically acceptable salt and (b) more than one member selected from the group consisting of following (i) to (v):

(i) a hydroxycarboxylic acid consisting of tartaric acid, maleic acid, and citric acid or an ester thereof;

(ii) an enolic acid consisting of ascorbic acid or erythorbic acid;

(iii) an aromatic carboxyl compound consisting of phthalic acid or propyl gallate or an ester thereof; and (iv) a carboxyl group-containing high-molecular substance consisting of carboxymethyl cellulose or alginic acid, (v) one or more additives selected from the group consisting of excipients, binders, disintegrating agents, sour agents, blowing agents, artificial sweeteners, flavors, lubricants and coloring agents, wherein tartaric acid, maleic acid, or citric acid, or an ester thereof, is compounded;

the one more members (i) to (iv) are present in an amount of 0.01 to 90 percent by weight based on total weight of the composition; and ramosetron or its pharmaceutically acceptable salt is present in an amount of 0.002 to 0.02 mg based on total weight of the composition.

5. The method of claim 3 further comprising admixing the one or more members with ramosetron or a pharmaceutically acceptable salt thereof.

6. The method of claim 4 further comprising admixing the one or more members with ramosetron or a pharmaceutically acceptable salt thereof.

7. The drug composition of claim 1 wherein one or more members (i) to (vi) are present in an amount of 0.1 to 10 percent by weight based on total weight of the composition.

8. An oral solid drug composition in solid dosage form comprising:

(a) ramosetron or a pharmaceutically acceptable salt thereof in an amount of 0.0008 to 0.1 percent by weight based on total weight of the composition;

(b) more than one member selected from the group consisting of following (i) to (vii) in an amount of 0.01 to 90 percent by weight based on total weight of the composition:

(i) an aliphatic carboxylic acid consisting of maleic acid, malonic acid, succinic acid, and fumaric acid, or an ester thereof, (ii) a hydroxycarboxylic acid consisting of tartaric acid, maleic acid, and citric acid or an ester thereof;

(iii) an acidic amino acid consisting of aspartic acid or glutamic acid;

(iv) an enolic acid consisting of ascorbic acid or erythorbic acid;

(v) an aromatic carboxyl compound consisting of phthalic acid or propyl gallate or an ester thereof; and (vi) a carboxyl group-containing high-molecular substance consisting of carboxymethyl cellulose or alginic acid, (vii) one or more additives selected from the group consisting of excipients, binders, disintegrating agents, sour agents, blowing agents, artificial sweeteners, flavors, lubricants and coloring agents, wherein tartaric acid, maleic acid, or citric acid, or an ester thereof, is present in the composition from 0.1 to 1.0 percent by weight based on total weight of the composition;

and (c) a light stabilizer agent selected from one or more of yellow iron sesquioxide, red iron sesquioxide and titanium oxide in an amount of 1 to 10 percent by weight based on total weight of the composition.

9. The drug composition of claim 8 wherein ramosetron or a pharmaceutically acceptable salt thereof is present in an amount of 0.002 to 0.02 mg based on total weight of the composition.

10. The drug composition of claim 8 wherein one or more members (i) to (vi) are present in an amount of 0.1 to 50 percent by weight based on total weight of the composition.

11. The drug composition of claim 8 wherein one or more members (i) to (vi) are present in an amount of 0.1 to 10 percent by weight based on total weight of the composition.

12. The drug composition of claim 8 wherein the light stabilizer agent is present in an amount of 0.05 to 2 percent by weight based on total weight of the composition.

13. An oral solid drug composition in solid dosage form comprising:

(a) ramosetron or a pharmaceutically acceptable salt thereof in an amount of 0.0008 to 0.1 percent by weight based on total weight of the composition;

(b) more than one member selected from the group consisting of following (i) to (vii) in an amount of 0.01 to 90 percent by weight based on total weight of the composition:

(i) an aliphatic carboxylic acid consisting of maleic acid, malonic acid, succinic acid, and fumaric acid, or an ester thereof, (ii) a hydroxycarboxylic acid consisting of tartaric acid, maleic acid, and citric acid or an ester thereof;

(iii) an acidic amino acid consisting of aspartic acid or glutamic acid;

(iv) an enolic acid consisting of ascorbic acid or erythorbic acid;

(v) an aromatic carboxyl compound consisting of phthalic acid or propyl gallate or an ester thereof; and (vi) a carboxyl group-containing high-molecular substance consisting of carboxymethyl cellulose or alginic acid, (vii) one or more additives selected from the group consisting of excipients, binders, disintegrating agents, sour agents, blowing agents, artificial sweeteners, flavors, lubricants and coloring agents, wherein tartaric acid, maleic acid, or citric acid, or an ester thereof, is present in the composition from 0.1 to 1.0 percent by weight based on total weight of the composition;

and (c) a light stabilizer agent selected from one or more of yellow iron sesquioxide, red iron sesquioxide and titanium oxide in an amount of 0.1 to 20 percent by weight based on total weight of the composition.

14. The drug composition of claim 13 wherein ramosetron or a pharmaceutically acceptable salt thereof is present in an amount of 0.002 to 0.02 mg based on total weight of the composition.

15. The drug composition of claim 13 wherein one or more members (i) to (vi) are present in an amount of 0.01 to 50 percent by weight based on total weight of the composition.

16. The drug composition of claim 13 wherein one or more members (i) to (vi) are present in an amount of 0.1 to 10 percent by weight based on total weight of the composition.

17. The drug composition of claim 16 wherein the light stabilizer agent is present in an amount of 0.2 to 10 percent by weight based on total weight of the composition.

18. The drug composition of claim 17 wherein the light stabilizer agent is present in an amount of 0.2 to 5 percent by weight based on total weight of the composition.

19. The drug composition of claim 1, further comprising a light stabilizer.

20. The method of claim 3, further comprising compounding a light stabilizer.

21. The drug composition of claim 19 wherein the light stabilizer comprises one or two or more members selected from the group consisting of yellow iron sesquioxide, red iron sesquioxide, and titanium oxide.

22. The method of claim 20 wherein the light stabilizer comprises one or more members selected from the group consisting of yellow iron sesquioxide, red iron sesquioxide, and titanium oxide.

23. The drug composition of claim 19 wherein the light stabilizer agent is present in an amount of 0.01 to 10 percent by weight based on total weight of the composition.

24. The drug composition of claim 19 wherein the light stabilizer agent is present in an amount of 0.05 to 2 percent by weight based on total weight of the composition.

25. The drug composition of claim 19 wherein the light stabilizer agent is present in an amount of 0.1 to 20 percent by weight based on total weight of the composition.

26. The drug composition of claim 19 wherein the light stabilizer agent is present in an amount of 0.2 to 10 percent by weight based on total weight of the composition.

27. The drug composition of claim 19 wherein the light stabilizer agent is present in an amount of 0.2 to 5 percent by weight based on total weight of the composition.

* * * * *